(12) United States Patent
Keeler et al.

(10) Patent No.: US 7,550,430 B2
(45) Date of Patent: Jun. 23, 2009

(54) CATIONIC ANTIMICROBIAL PEPTIDES AND COMPOSITIONS

(75) Inventors: Sharon J. Keeler, Bear, DE (US); Helen S. M. Lu, Wallingford, PA (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 383 days.

(21) Appl. No.: 10/920,548

(22) Filed: Aug. 18, 2004

(65) Prior Publication Data

US 2005/0065072 A1  Mar. 24, 2005

Related U.S. Application Data

(60) Provisional application No. 60/496,123, filed on Aug. 18, 2003.

(51) Int. Cl.
A61K 38/00 (2006.01)
A61K 38/12 (2006.01)

(52) U.S. Cl. .......................................... 514/9; 530/317

(58) Field of Classification Search ....................... None
See application file for complete search history.

(56) References Cited

U.S. PATENT DOCUMENTS

| 5,593,866 A | 1/1997 | Hancock et al. |
| 5,847,047 A | 12/1998 | Haynie |
| 6,638,531 B1 | 10/2003 | Van Nieuw Amerongen et al. |
| 6,835,536 B2 | 12/2004 | Krieger et al. |
| 2003/0171281 A1 | 9/2003 | Krieger et al. |
| 2004/0019181 A1 | 1/2004 | Falla et al. |

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976) 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Michael Zasloff, Multicellular organisms live, by and large, harmoniously with microbes. The cornea of the eye of an animal is almost always free of signs of infection. The insect flourishes without lymphocytes or antibodies. A plant seed germinates successfully in the midst of soil microbes. How is this accomplished? Both animals and plants possess potent, broad-spectrum antimicrobial peptides, which they use to fend off a wide range of microbes, including bacteria, fungi, viruses and protozoa. What sorts of molecules are they? How are they employed by animals in their defence? As our need for new antibodies antibiotics becomes more pressing, could we design anti-infective drugs based on the design principles these molecules teach us?, Nature, vol. 415:389-395, Jan. 24, 2002.
Richard M. Epand and Hans J. Vogel, Diversity of antimicrobial peptides and their mechanisms of action, Biochimica et Biophysica Acta, vol. 1462:11-28, Oct. 5, 1999.

* cited by examiner

*Primary Examiner*—Anish Gupta
*Assistant Examiner*—Marcela M Cordero Garcia
(74) *Attorney, Agent, or Firm*—Christine M. Lhulier

(57) ABSTRACT

The invention described herein relates to compositions of novel antimicrobial peptides. The peptides of the present invention exhibit high antibacterial activity and low hemolytic activity. The invention further provides compositions comprising these antimicrobial peptides and methods of use thereof for killing, reducing the growth of, or preventing the growth of microorganisms. The invention also provides antimicrobial substrates and articles comprising the peptides of the present invention.

46 Claims, No Drawings

SEQUENCE LISTING

```
<160> NUMBER OF SEQ ID NOS: 43

<210> SEQ ID NO 1
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 1

Lys Gly Leu Lys Lys Leu Leu Lys Gly Leu Lys Lys Leu Leu Lys Leu
1               5                   10                  15

<210> SEQ ID NO 2
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 2

Lys Gly Leu Lys Lys Gly Leu Lys Leu Leu Lys Lys Leu Leu Lys Leu
1               5                   10                  15

<210> SEQ ID NO 3
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 3

Lys Gly Leu Lys Lys Leu Leu Lys Leu Gly Lys Lys Leu Leu Lys Leu
1               5                   10                  15

<210> SEQ ID NO 4
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 4
```

```
Lys Gly Leu Lys Lys Leu Gly Lys Leu Leu Lys Lys Leu Leu Lys Leu
1               5                   10                  15
```

<210> SEQ ID NO 5
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 5

```
Lys Gly Leu Lys Lys Leu Leu Lys Leu Leu Lys Lys Gly Leu Lys Leu
1               5                   10                  15
```

<210> SEQ ID NO 6
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 6

```
Lys Gly Leu Lys Lys Leu Leu Lys Leu Leu Lys Lys Leu Gly Lys Leu
1               5                   10                  15
```

<210> SEQ ID NO 7
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 7

```
Lys Cys Leu Lys Lys Leu Leu Lys Leu Gly Lys Leu Leu Lys Lys Leu
1               5                   10                  15
```

<210> SEQ ID NO 8
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 8

```
Lys Cys Leu Lys Lys Gly Leu Lys Leu Leu Lys Lys Leu Leu Lys Leu
1               5                   10                  15
```

<210> SEQ ID NO 9
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 9

```
Lys Cys Leu Lys Lys Leu Leu Lys Gly Leu Lys Lys Leu Leu Lys Leu
1               5                   10                  15
```

<210> SEQ ID NO 10
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 10

```
Lys Cys Leu Lys Lys Leu Gly Lys Leu Leu Lys Lys Leu Leu Lys Leu
```

<210> SEQ ID NO 11
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 11

Lys Cys Leu Lys Lys Leu Gly Lys Leu Leu Lys Lys Leu Gly Lys Leu
1               5                   10                  15

<210> SEQ ID NO 12
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 12

Lys Cys Leu Lys Lys Gly Leu Lys Leu Leu Lys Lys Leu Leu Lys Gly
1               5                   10                  15

<210> SEQ ID NO 13
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 13

Lys Gly Leu Lys Lys Leu Leu Lys Leu Leu Lys Lys Leu Leu Lys Leu
1               5                   10                  15

<210> SEQ ID NO 14
<211> LENGTH: 17
<212> TYPE: PRT
<213> ORGANISM: artificial sequence
<220> FEATURE:
<223> OTHER INFORMATION: Synthetic amino acid sequence

<400> SEQUENCE: 14

Lys Cys Leu Lys Lys Leu Leu Lys Leu Gly Lys Lys Leu Leu Lys Leu
1               5                   10                  15

Cys

<210> SEQ ID NO 15
<211> LENGTH: 17
<212> TYPE: PRT
<213> ORGANISM: artificial sequence
<220> FEATURE:
<223> OTHER INFORMATION: Synthetic amino acid sequence

<400> SEQUENCE: 15

Lys Cys Leu Lys Lys Gly Leu Lys Leu Leu Lys Lys Leu Leu Lys Leu
1               5                   10                  15

Cys

<210> SEQ ID NO 16
<211> LENGTH: 17
<212> TYPE: PRT
<213> ORGANISM: artificial sequence
<220> FEATURE:
<223> OTHER INFORMATION: Synthetic amino acid sequence

```
<400> SEQUENCE: 16

Lys Cys Leu Lys Lys Leu Leu Lys Leu Leu Lys Leu Gly Lys Leu
1               5                   10                  15

Cys

<210> SEQ ID NO 17
<211> LENGTH: 17
<212> TYPE: PRT
<213> ORGANISM: artificial sequence
<220> FEATURE:
<223> OTHER INFORMATION: Synthetic amino acid sequence

<400> SEQUENCE: 17

Lys Cys Leu Lys Lys Leu Leu Lys Leu Leu Lys Lys Gly Leu Lys Leu
1               5                   10                  15

Cys

<210> SEQ ID NO 18
<211> LENGTH: 17
<212> TYPE: PRT
<213> ORGANISM: artificial sequence
<220> FEATURE:
<223> OTHER INFORMATION: Synthetic amino acid sequence

<400> SEQUENCE: 18

Lys Cys Leu Lys Lys Leu Leu Lys Gly Leu Lys Lys Leu Leu Lys Leu
1               5                   10                  15

Cys

<210> SEQ ID NO 19
<211> LENGTH: 17
<212> TYPE: PRT
<213> ORGANISM: artificial sequence
<220> FEATURE:
<223> OTHER INFORMATION: Synthetic amino acid sequence

<400> SEQUENCE: 19

Lys Cys Leu Lys Lys Leu Gly Lys Leu Leu Lys Lys Leu Leu Lys Leu
1               5                   10                  15

Cys

<210> SEQ ID NO 20
<211> LENGTH: 17
<212> TYPE: PRT
<213> ORGANISM: artificial sequence
<220> FEATURE:
<223> OTHER INFORMATION: Synthetic amino acid sequence

<400> SEQUENCE: 20

Lys Cys Leu Lys Lys Leu Gly Lys Leu Leu Lys Lys Leu Leu Lys Gly
1               5                   10                  15

Cys

<210> SEQ ID NO 21
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 21

Cys Leu Lys Lys Leu Leu Lys Leu Gly Lys Lys Leu Leu Lys Leu Cys
1               5                   10                  15
```

<210> SEQ ID NO 22
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 22

Cys Leu Lys Lys Gly Leu Lys Leu Leu Lys Leu Leu Lys Leu Leu Cys
1               5                   10                  15

<210> SEQ ID NO 23
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 23

Cys Leu Lys Lys Leu Leu Lys Leu Leu Lys Lys Leu Gly Lys Leu Cys
1               5                   10                  15

<210> SEQ ID NO 24
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 24

Cys Leu Lys Lys Leu Leu Lys Leu Leu Lys Lys Gly Leu Lys Leu Cys
1               5                   10                  15

<210> SEQ ID NO 25
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 25

Cys Leu Lys Lys Leu Leu Lys Gly Leu Lys Lys Leu Leu Lys Leu Cys
1               5                   10                  15

<210> SEQ ID NO 26
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 26

Cys Leu Lys Lys Leu Gly Lys Leu Leu Lys Lys Leu Leu Lys Leu Cys
1               5                   10                  15

<210> SEQ ID NO 27
<211> LENGTH: 17
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (2)..(17)

<400> SEQUENCE: 27

Lys Cys Leu Lys Lys Leu Leu Lys Leu Gly Lys Lys Leu Leu Lys Leu
1               5                   10                  15

Cys

<210> SEQ ID NO 28
<211> LENGTH: 17
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (2)..(17)

<400> SEQUENCE: 28

Lys Cys Leu Lys Lys Gly Leu Lys Leu Leu Lys Lys Leu Leu Lys Leu
1               5                   10                  15

Cys

<210> SEQ ID NO 29
<211> LENGTH: 17
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (2)..(17)

<400> SEQUENCE: 29

Lys Cys Leu Lys Lys Leu Leu Lys Leu Leu Lys Lys Leu Gly Lys Leu
1               5                   10                  15

Cys

<210> SEQ ID NO 30
<211> LENGTH: 17
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (2)..(17)

<400> SEQUENCE: 30

Lys Cys Leu Lys Lys Leu Leu Lys Leu Leu Lys Lys Gly Leu Lys Leu
1               5                   10                  15

Cys

<210> SEQ ID NO 31
<211> LENGTH: 17
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (2)..(17)

<400> SEQUENCE: 31

Lys Cys Leu Lys Lys Leu Leu Lys Gly Leu Lys Lys Leu Leu Lys Leu
1               5                   10                  15

Cys

<210> SEQ ID NO 32

```
<211> LENGTH: 17
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (2)..(17)

<400> SEQUENCE: 32

Lys Cys Leu Lys Lys Leu Gly Lys Leu Leu Lys Lys Leu Leu Lys Leu
1               5                   10                  15

Cys

<210> SEQ ID NO 33
<211> LENGTH: 17
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (2)..(17)

<400> SEQUENCE: 33

Lys Cys Leu Lys Lys Leu Gly Lys Leu Leu Lys Lys Leu Leu Lys Gly
1               5                   10                  15

Cys

<210> SEQ ID NO 34
<211> LENGTH: 16
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (1)..(16)

<400> SEQUENCE: 34

Cys Leu Lys Lys Leu Leu Lys Leu Gly Lys Lys Leu Leu Lys Leu Cys
1               5                   10                  15

<210> SEQ ID NO 35
<211> LENGTH: 16
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (1)..(16)

<400> SEQUENCE: 35

Cys Leu Lys Lys Gly Leu Lys Leu Leu Lys Lys Leu Leu Lys Leu Cys
1               5                   10                  15

<210> SEQ ID NO 36
<211> LENGTH: 16
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (1)..(16)

<400> SEQUENCE: 36
```

Cys Leu Lys Lys Leu Leu Lys Leu Leu Lys Lys Leu Gly Lys Leu Cys
1               5                   10                  15

<210> SEQ ID NO 37
<211> LENGTH: 16
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (1)..(16)

<400> SEQUENCE: 37

Cys Leu Lys Lys Leu Leu Lys Leu Leu Lys Lys Gly Leu Lys Leu Cys
1               5                   10                  15

<210> SEQ ID NO 38
<211> LENGTH: 16
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (1)..(16)

<400> SEQUENCE: 38

Cys Leu Lys Lys Leu Leu Lys Gly Leu Lys Leu Leu Lys Leu Cys
1               5                   10                  15

<210> SEQ ID NO 39
<211> LENGTH: 16
<212> TYPE: PRT
<213> ORGANISM: artificial sequence
<220> FEATURE:
<223> OTHER INFORMATION: Synthetic amino acid sequence
<220> FEATURE:
<221> NAME/KEY: DISULFID
<222> LOCATION: (1)..(16)

<400> SEQUENCE: 39

Cys Leu Lys Lys Leu Gly Lys Leu Leu Lys Lys Leu Leu Lys Leu Cys
1               5                   10                  15

<210> SEQ ID NO 40
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 40

Lys Gly Leu Lys Lys Gly Leu Lys Gly Leu Lys Lys Leu Leu Lys Leu
1               5                   10                  15

<210> SEQ ID NO 41
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 41

Lys Gly Leu Lys Lys Leu Leu Lys Ala Leu Lys Lys Leu Leu Lys Leu
1               5                   10                  15

<210> SEQ ID NO 42

```
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 42

Lys Gly Leu Lys Lys Leu Gly Lys Leu Leu Lys Lys Leu Leu Lys Leu
1               5                   10                  15

<210> SEQ ID NO 43
<211> LENGTH: 16
<212> TYPE: PRT
<213> ORGANISM: artificial sequence
<220> FEATURE:
<223> OTHER INFORMATION: Synthetic amino acid sequence

<400> SEQUENCE: 43

Lys Gly Gly Lys Lys Leu Leu Lys Gly Leu Lys Lys Leu Leu Lys Leu
1               5                   10                  15
```

CATIONIC ANTIMICROBIAL PEPTIDES AND COMPOSITIONS

FIELD OF THE INVENTION

This invention relates to compositions of cationic, antimicrobial oligopeptides, to methods for producing and using the compositions, and to articles comprising the compositions. The antimicrobial oligopeptides of the present invention are useful in pharmaceutical, healthcare, medical device, industrial, food, agricultural, and personal care applications.

TECHNICAL BACKGROUND OF THE INVENTION

Antimicrobial peptides (AMPs) are ubiquitous in nature and play an important role in the innate immune system of many species (Zasloff, M., Nature (2002) 415:389-395; Epand, R. M., and Vogel, H. J., Biochim Biophys Acta (1999) 1462:11-28). Antimicrobial peptides are diverse in structure, function, and specificity. The biological activity of antimicrobial peptides ranges from broad spectrum (active against both Gram positive and Gram negatives) and non-hemolytic (e.g., magainin) to broad spectrum and highly hemolytic (e.g., melittin). For commercial applications of AMPs, it is desirable to increase the bactericidal activity and decrease the hemolytic activity.

One major class of antimicrobial peptides consists of linear α-helical peptides, such as cecropin and magainin. Haynie (U.S. Pat. No. 5,847,047) described synthetic peptides based on a heptad repeat and comprised of Leu and Lys residues that were designed to adopt an α-helical amphiphilic structure. These peptides exhibited activity at 8-63 μg/mL against *Escherichia coli* and *Staphylococcus aureus* in solution, however they also exhibited moderate hemolytic activity.

SUMMARY OF THE INVENTION

The present invention provides antimicrobial peptides represented by Formula I:

$$(B)-(U)-(Z-B-B-Z-Z-B-Z)_n(U) \quad \text{Formula (I)}$$

wherein B, U and Z represent natural or unnatural amino acids and wherein:
(a) Z is independently selected from Gly or a hydrophobic amino acid selected from the group consisting of Leu, Ile, Trp, Phe, Val, Met, and Ala; and
  (i) when Z is Gly, the Gly residues representing Z must be minimally 7 amino acid residues apart; and
  (ii) no more than six sequential hydrophobic Z residues may occur in the antimicrobial peptide;
(b) B is a cationic amino acid independently selected from the group consisting of Lys, Arg, His, Orn, Har, and Dbu; and
(c) U is Gly, Cys or Cys(R), wherein R is a protecting group on the Cys thiol;
(d) n=2-8; and
(e) the N-terminal B residue, and the N-terminal or C-terminal U residue, are optionally part of the antimicrobial peptide.

The present invention also provides antimicrobial peptides represented by Formula II:

wherein B and Z represent natural or unnatural amino acids and wherein:

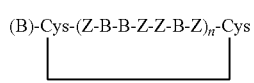

$$\text{(B)-Cys-(Z-B-B-Z-Z-B-Z)}_n\text{-Cys} \quad \text{Formula (II)}$$

(a) Z is independently selected from Gly or a hydrophobic amino acid selected from the group consisting of Leu, Ile, Trp, Phe, Val, Met, and Ala; and
  (i) when Z is Gly, the Gly residues representing Z must be minimally 7 amino acid residues apart; and
  (ii) no more than six sequential hydrophobic Z residues may occur in the antimicrobial peptide;
(b) B is a cationic amino acid independently selected from the group consisting of Lys, Arg, His, Orn, Har, and Dbu;
(c) n=2-5;
(d) the N-terminal B residue is optionally part of the antimicrobial peptide; and
(e) the antimicrobial peptide contains a disulfide bridge formed intramolecularly between the Cys residues.

BRIEF DESCRIPTIONS OF SEQUENCES

The sequence descriptions and content of the sequence listing attached hereto (additionally provided in a computer readable form) are incorporated by reference as a part of this application. The sequences and Sequence Listing comply with the rules governing nucleotide and/or amino acid sequence disclosures in patent applications as set forth in 37 C.F.R. §1.821-1.825 ("Requirements for Patent Applications Containing Nucleotide Sequences and/or Amino Acid Sequence Disclosures—The Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

SEQ ID NOs:1 to 43 are peptides according to Formula (I) or Formula (II).

DETAILED DESCRIPTION OF THE INVENTION

The invention described herein provides compositions of novel antimicrobial peptides based on heptad repeating units that comprise hydrophobic, cationic, hydrophilic, and helix-disrupting residues. The peptides of the present invention exhibit high antibacterial activity and low hemolytic activity. The invention further provides compositions comprising these antimicrobial peptides and methods of use thereof for killing, reducing the growth of, or preventing the growth of microorganisms. The invention also provides substrates and articles comprising the antimicrobial peptides of the present invention.

Definitions and Abbreviations:

In this disclosure, a number of terms and abbreviations are used. The following definitions are provided.

The terms "peptide" and "oligopeptide" will be used interchangably and will refer to amino acid sequences of between two and thirty amino acids in length.

The term "antimicrobial" means having to do with the killing, growth inhibition or growth prevention of microorganisms. "Growth inhibition" means reduced growth of the microorganisms. "Growth prevention" means that growth is stopped.

The term "microorganism" or "microbe" is meant to include any organism comprised of the phylogenetic domains bacteria and archaea, as well as unicellular and filamentous fungi (such as yeasts and molds), unicellular and filamentous algae, unicellular and multicellular parasites, and viruses.

The term "cytotoxic" means the killing or lysis of eukaryotic organisms.

The terms "amphiphilic helix" and "amphipathic helix" are used interchangably and mean any protein or peptide secondary structure that forms a helix wherein that helix includes both hydrophobic and hydrophilic regions and demonstrates an affinity for hydrophillic structures such as those found in lipid bilayers and cell membranes.

A "substrate coated with an effective amount of an antimicrobial composition" means applying to the surface a composition comprising an antimicrobial peptide in an amount effective to kill, inhibit or prevent the growth of microorganisms.

The term "MIC" refers to minimal inhibitory concentration and will be defined as the lowest concentration of either soluble peptide or peptide immobilized on a polymer that results in total kill of bacteria.

"Reverse phase high performance liquid chromatography" is abbreviated RP-HPLC.

"ATCC" refers to the American Type Culture Collection International Depositary located at 10801 University Boulevard, Manassas, Va. 20110-2209, U.S.A. The "ATCC No." is the accession number to cultures on deposit with the ATCC.

Ornithine is abbreviated "Orn", homoarginine is abbreviated "Har", and 2,4-diaminobutyric acid is abbreviated "Dbu".

As used herein the following abbreviations will be used to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamine acid | Glu | E |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention provides antimicrobial peptides of structural Formula (I):

    Formula (I)

wherein B, U and Z represent natural or unnatural amino acids and wherein:

(a) Z is independently selected from Gly or a hydrophobic amino acid selected from the group consisting of Leu, Ile, Trp, Phe, Val, Met, and Ala; and
  (i) when Z is Gly, the Gly residues representing Z must be minimally 7 amino acid residues apart; and
  (ii) no more than six sequential hydrophobic Z residues may occur in the antimicrobial peptide;
(b) B is a cationic amino acid independently selected from the group consisting of Lys, Arg, His, Orn, Har, and Dbu; and
(c) U is Gly, Cys or Cys(R), wherein R is a protecting group on the Cys thiol;
(d) n=2-8; and
(e) the N-terminal B residue, and the N-terminal or C-terminal U residue, are optionally part of the antimicrobial peptide.

In peptides of the invention, R is a thiol protecting group such as acetamidomethyl (Acm), methyl methane thiosulfonate, or other cysteine-protecting group known to those skilled in the art.

The present invention also provides antimicrobial peptides of structural Formula (II):

wherein B and Z represent natural or unnatural amino acids and

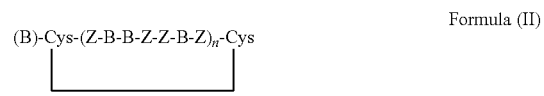    Formula (II)

wherein:
(a) Z is independently selected from Gly or a hydrophobic amino acid selected from the group consisting of Leu, Ile, Trp, Phe, Val, Met, and Ala; and
  (i) when Z is Gly, the Gly residues representing Z must be minimally 7 amino acid residues apart; and
  (ii) no more than six sequential hydrophobic Z residues may occur in the antimicrobial peptide;
(b) B is a cationic amino acid independently selected from the group consisting of Lys, Arg, His, Orn, Har, and Dbu;
(c) n=2-5;
(d) the N-terminal B residue is optionally part of the antimicrobial peptide; and
(e) the antimicrobial peptide contains a disulfide bridge formed intramolecularly between the Cys residues.

In another embodiment of the invention, Z in Formulae (I) and (II) may be a neutral hydrophilic residue, with the provision that no more than one neutral hydrophilic residue may be substituted per core peptide. The core peptide in Formulas (I) and (II) is represented by (Z-B-B-Z-Z-B-Z). The neutral hydrophilic residue is selected from the group consisting of Thr, Ser, Asn, Gln, and Tyr.

In another embodiment, B in Formulas (I) and (II) may be a charged anionic residue, with the provision that no more than one anionic residue is present per twelve sequential amino acid residues. The charged anionic residue is selected from the group consisting of Asp and Glu.

In another embodiment, the invention provides a peptide according to Formula (I) wherein B and/or U are optionally present on the N-terminus, and additionally Z is deleted. In another embodiment, the invention provides a peptide according to Formula (I) wherein U is optionally present on the C-terminus, and additionally Z and/or B is deleted.

The preferred hydrophobic residues in Formulas (I) and (II) are Leu, Ile, Phe, Ala, and Val; the most preferred hydrophobic residue is Leu. The preferred cationic residues are Lys and Arg; the most preferred cationic residue is Lys.

The most preferred peptides of the present invention include peptides of the following sequences wherein n=2:

| Sequence | |
|---|---|
| KGLKKLLKGLKKLLKL | (SEQ ID NO:1) |
| KGLKKGLKLLKKLLKL | (SEQ ID NO:2) |
| KGLKKLLKLGKKLLKL | (SEQ ID NO:3) |
| KGLKLGKLLKKLLKL | (SEQ ID NO:4) |
| KGLKKLLKLLKKGLKL | (SEQ ID NO:5) |
| KGLKKLLKLLKKLGKL | (SEQ ID NO:6) |
| KCLKKLLKLGKKLLKL | (SEQ ID NO:7) |
| KCLKKGLKLLKKLLKL | (SEQ ID NO:8) |
| KCLKKLLKGLKKLLKL | (SEQ ID NO:9) |
| KCLKKLGKLLKKLLKL | (SEQ ID NO:10) |
| KCLKKLGKLLKKLGKL | (SEQ ID NO:11) |
| KCLKKGLKLLKKLLKG | (SEQ ID NO:12) |
| KGLKKLLKLLKKLLKL | (SEQ ID NO:13) |
| KCLKKLLKLGKKLLKLC | (SEQ ID NO:14) |
| KCLKKGLKLLKKLLKLC | (SEQ ID NO:15) |
| KCLKKLLKLLKKLGKLC | (SEQ ID NO:16) |
| KCLKKLLKLLKKGLKLC | (SEQ ID NO:17) |
| KCLKKLLKGLKKLLKLC | (SEQ ID NO:18) |
| KCLKKLGKLLKKLLKLC | (SEQ ID NO:19) |
| KCLKKLGKLLKKLLKGC | (SEQ ID NO:20) |
| CLKKLLKLGKKLLKLC | (SEQ ID NO:21) |
| CLKKGLKLLKKLLKLC | (SEQ ID NO:22) |
| CLKKLLKLLKKLGKLC | (SEQ ID NO:23) |
| CLKKLLKLLKKGLKLC | (SEQ ID NO:24) |
| CLKKLLGLKKLLKLC | (SEQ ID NO:25) |
| CLKKLGKLLKKLLKLC | (SEQ ID NO:26) |
| KCLKKLLKLGKKLLKLC | (SEQ ID NO:27) |
| KCLKKGLKLLKKLLKLC | (SEQ ID NO:28) |
| KCLKKLLKLLKKLGKLC | (SEQ ID NO:29) |
| KCLKKLLKLLKKGLKLC | (SEQ ID NO:30) |
| KCLKKLLKGLKKLLKLC | (SEQ ID NO:31) |
| KCLKKLGKLLKKLLKLC | (SEQ ID NO:32) |
| KCLKKLGKLLKKLLKGC | (SEQ ID NO:33) |
| CLKKLLKLGKKLLKLC | (SEQ ID NO:34) |
| CLKKGLKLLKKLLKLC | (SEQ ID NO:35) |
| CLKKLLKLLKKLGKLC | (SEQ ID NO:36) |
| CLKKLLKLLKKGLKLC | (SEQ ID NO:37) |
| CLKKLLKGLKKLLKLC | (SEQ ID NO:38) |
| CLKKLGKLLKKLLKLC | (SEQ ID NO:39) |
| KGLKKLLKALKKLLKL | (SEQ ID NO:41) |
| KGLKKLGKLLKKLLKL | (SEQ ID NO:42) |
| KGGKKLLKGLKKLLKL | (SEQ ID NO:43) |

The most preferred peptides include SEQ ID NOs 1-39 and 41 to 43, wherein the peptides are optionally modified on the N-terminus with an acetyl group, on the C-terminus with an amide group, or a combination thereof. The most preferred peptides also include SEQ ID NOs 7-12 and 14-25 wherein the cysteine residues are optionally modified with a thiol-protecting group such as an Acm group or methylmethane thiosulfonate group.

Further highly preferred peptides include SEQ ID NOs 1-39 and 41 to 43, wherein one or more K residues is replaced with R. Further highly preferred peptides also include SEQ ID NOs 1-39 and 41 to 43, wherein one or more L residues is replaced with F, I, A, or V. Further highly preferred peptides include SEQ ID NOs 1-39 and 41 to 43, wherein one or more K residues is replaced with R, and wherein one or more L residues is replaced with F, I, A, or V. Further highly preferred peptides are those in which the hydrophobic residues are selected from the group consisting of Leu, Phe, Ala, and Val; the cationic residues are Lys or Arg; the U group in Formula (I) is Gly, Cys, or Cys(R); and n=3.

The peptides of the invention may be synthesized by solid-phase synthesis, solution-phase synthesis or recombinant biosynthesis.

Solid-Phase and Solution-Phase Synthesis

The peptides of the present invention may be synthesized by methods that are well known in the art. For example, the peptides may be synthesized by solid-phase synthesis as originally described by Merrifield (J. Am. Chem. Soc. (1982) 85:2149-2154), or by Stewart (Solid Phase Peptide Synthesis ($2^{nd}$ ed); Pierce Chemical Company, Rockford, Ill., 1984), or as described in detail in Peptides: Synthesis, Structures and Applications (Gutte (ed.), (1995) Academic Press, New York), and Chemical Approaches to the Synthesis of Peptides and Proteins (Lloyd-Willimas, P., Alberico, G., Giralt, E. (eds.) (1997) CRC Press, New York). By using standard peptide synthesis methodology, it would be possible to substitute unnatural amino acids, such as D-amino acids, for natural amino acids to enhance the stability or efficacy of the peptide in a manufactured product.

The peptides of the present invention may also be synthesized by solution-phase synthesis according to methods detailed in Chemical Approaches to the Synthesis of Peptides and Proteins (Lloyd-Willimas, P., Alberico, G., Giralt, E. (eds.) (1997) CRC Press, New York) and The Practice of Peptide Synthesis (Bodanszky, M., and Bodanszky, A. (ed.), (1984) Springer-Verlag, New York). For large-scale peptide synthesis, the shorter the length of the peptide sequence, the more amenable it is to large scale solution-phase synthesis (Andesson, et al. Biopolymers (Peptide Science), (2000) 55:227-250).

Recombinant Biosynthesis:

The peptides of the present invention may also be synthesized by recombinant methods of synthesis. Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989); and by Silhavy, T. J., Bennan, M. L. and Enquist, L. W., *Experiments with Gene Fusions*, Cold Spring Harbor Laboratory Cold Press Spring Harbor, N.Y. (1984); Ausubel, F. M. et al., *Current Protocols in Molecular Biology*, published by Greene Publishing Assoc. and Wiley-Interscience (1987) and PCR Protocols: Current Methods and Applications, Humana Press, Inc., Totowa, N.J. Methods for recombinant synthesis of the peptides of the invention are also described in U.S. Patent Application No. 60/496,122, which is incorporated herein by reference.

Methods for recombinant synthesis of the peptides of the present invention include the preparation of synthetic genes by, for example, in vitro chemical synthesis of the genes using conventional methods as known in the art. "Synthetic genes" can be assembled from oligonucleotide building blocks that are chemically synthesized using procedures known to those skilled in the art. These building blocks are ligated and annealed to form gene segments that are then enzymatically assembled to construct the entire gene. The oligonucleotides necessary may be determined by back-translating from the amino acid sequence of the peptide being synthesized.

"Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Various commercial synthetic apparatuses are available, such as the automated synthesizer from Applied Biosystems (Foster City, Calif.). Accordingly, the coding sequences can be tailored for optimal gene expression based on optimization of nucleotide sequence to reflect the "codon bias" of the host cell. The skilled artisan is well aware of the codon-bias exhibited by a specific host cell in usage of nucleotide codons to specify a given amino acid. Therefore, when synthesizing a gene for expression in a host cell, it is desirable to design the gene such that its frequency of codon usage approaches the frequency of preferred codon usage of the host cell. The skilled artisan appreciates the likelihood of successful gene expression if codon usage is biased towards those codons favored by the host. Determination of preferred codons can be based on a survey of genes derived from the host cell where sequence information is available. Accordingly, in the instant invention, if *Escherichia coli* were used as the expression host, codon bias for enteric bacteria could be utilized as the basis for synthesizing the nucleic acid sequences encoding the antimicrobial peptide such that optimal peptide expression would be obtained in *E. coli*.

The synthetic genes may comprise, in addition to the peptide sequence, a fusion carrier peptide linked to the sequence encoding the antimicrobial peptide. The fusion carrier peptide may protect the host cell during expression from the toxic effects of the antimicrobial peptide. The fusion carrier peptide may also provide a signal sequence to direct export of an expressed antimicrobial peptide, or it may provide a means for subsequent purification of the expressed peptide.

The peptides may also be synthesized as concatemers within a gene. The term "concatemer" herein refers to multiple copies of a given unit as tandem repeats. The multiple copies (multimers) may be separated by intervening sequences that provide, for example, cleavage sites for post-expression peptide recovery. For example, a gene might comprise multiple copies of the peptide described by Formula I:

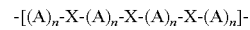

wherein X represents an intervening sequence between two or more copies of the $(A)_n$ sequence for the antimicrobial peptide.

In order to express the antimicrobial peptide in a suitable host cell, the DNA sequence encoding the peptide is operably linked to a suitable promoter. The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or antisense RNA derived from the nucleic acid fragment of the invention. Expression may also refer to translation of mRNA into a polypeptide.

The DNA sequence of the peptide may be operably linked to a promoter in a suitable vector, plasmid or cassette. The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The antimicrobial peptide may be expressed from the plasmid in a suitable host, or the gene encoding the peptide may be incorporated into the host's chromosome. Host cells preferred for expression of the instant genes and nucleic acid molecules are microbial hosts that can be found broadly within the fungal or bacterial families and which grow over a wide range of temperature, pH values, and solvent tolerances. For example, it is contemplated that any bacteria, yeast, algae and filamentous fungi will be suitable hosts for expression of the present nucleic acid fragments. Because transcription, translation, and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of suitable host strains include, but are not limited to: fungal or yeast species such as *Aspergillus, Trichoderma, Saccharomyces, Pichia, Candida* and *Hansenula*; or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium, Klebsiella, Burkholderia, Sphingomonas, Brevibacteium, Corynebacterium, Mycobacterium, Arthrobacter, Nocardia, Actinomyces*, and *Comamonas*.

Microbial expression systems and expression vectors containing regulatory sequences that direct high level expression of foreign proteins are well known to those skilled in the art. Any of these could be used to construct chimeric genes for production any of the gene products of the instant sequences. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell, are numerous and familiar to those skilled in the art. Virtually any promoter capable of driving these genes is suitable for the present invention including but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, IP$_L$, IP$_R$, T7, tac, and trc (useful for expression in *Escherichia coli*) as well as the amy, apr, and npr promoters, and various phage promoters useful for expression in *Bacillus*.

Termination control regions may also be derived from various genes native to the preferred hosts. Optionally, a termination site may be unnecessary; however, it is most preferred if included.

Plant Host Systems

The instant invention can also be used to transform a suitable plant host with the gene(s) encoding the antimicrobial peptides. Virtually any plant host that is capable of supporting the expression of an antimicrobial peptide gene will be suitable, however crop plants are preferred for their ease of harvesting and large biomass. Suitable plant hosts will include but are not limited to both monocots and dicots such as soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp.), barley (*Hordeum vulgare*), oats (*Avena sativa*, L), sorghum (*Sorghum bicolor*), rice (*Oryza sativa*), *Arabidopsis*, cruciferous vegetables, melons, carrots, celery, parsley, tomatoes, potatoes, strawberries, peanuts, grapes, grass seed crops, sugar beet, sugar cane, canola, millet, beans, peas, rye, flax, hardwood trees, softwood trees, and forage grasses.

Industrial Production of Recombinant Antimicrobial Peptides

Where commercial production of antimicrobial peptides is desired, a variety of culture methodologies may be applied. For example, large-scale production from a recombinant microbial host may be produced by both batch and continuous culture methodologies.

A classical batch culturing method is a closed system where the composition of the medium is set at the beginning of the culture and not subjected to artificial alterations during the culturing process. Thus, at the beginning of the culturing process the medium is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. The carbon substrates may also comprise, for example, alcohols, organic acids, proteins or hydrolyzed proteins, or amino acids. Additionally the carbon substrate may also be one-carbon substrates such as carbon dioxide or methane for which metabolic conversion into key biochemical intermediates has been demonstrated. In addition to one and two carbon substrates, methylotrophic organisms are also known to utilize a number of other carbon containing compounds such as methylamine and glucosamine, as well as methanol and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK).

Similarly, various species of *Candida* will metabolize alanine or oleic acid (Sulter et al., *Arch. Microbiol.*, 153:485A89 (1990)). Hence, it is contemplated that the source of carbon utilized in the present invention may encompass a wide variety of carbon containing substrates and will only be limited by the choice of organism.

Commercial production of antimicrobial peptides may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

As is well known to those skilled in the art, whole microbial cells can be used as catalyst without any pretreatment such as permeabilization. Alternatively, the whole cells may be permeabilized by methods familiar to those skilled in the art (e.g., treatment with toluene, detergents, or freeze thawing) to improve the rate of diffusion of materials into and out of the cells.

Applications

Oligopeptides produced by the present invention are effective as antimicrobials and can be employed to kill, inhibit the growth of, or prevent the growth of microorganisms such as Gram-positive bacteria, Gram-negative bacteria, viruses, and fungi. The peptides of the present invention are effective in antimicrobial compositions for use against disease-causing organisms in humans, animals, aquatic and avian species, and plants. The oligopeptides and compositions thereof can also be used as preservatives or sterilants for articles susceptible to microbial contamination. The oligopeptides of the present invention and compositions thereof can be administered to a target cell or host by direct or indirect application. For example, the peptide may be administered topically, systemically or as a coating. The peptides of the present invention and compositions thereof may also be bound to or incorporated into substrates to provide antimicrobial substrates to reduce or inhibit microbial contamination of the substrate. The present invention also provides articles comprising the antimicrobial substrates of the invention.

Substrates suitable for the present invention include polymers selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, and mixtures or blends thereof. Additional polymer substrates are also functionalized polymer substrates comprising the aforementioned polymers and that additionally contain, or may be functionalized to contain, active groups with which peptides may react, and which allow for immobilization of the peptides. Examples of active groups include, but are not limited to: acrylic acid, acetal, hydroxyl, amines, epoxides, carboxylates, anhydrides, isocyanates, thioisocyanates, azides, aldehydes, halides, acyl halides, aryl halides and ketones at 1 to 50% by weight of the polymer. Various methods of protein or peptide immobilization are described in Protein Immobilization (Richard F. Taylor (ed.), Marcel Dekker, New York, 1991).

Substrates suitable for the present invention also include ceramics, glass, metal, metal oxides, and composites comprised of ceramics, glass, metal or metal oxides plus polymers as described above. Suitable metals include steel, stainless steel, aluminum, copper, titanium, alloys thereof, and combinations thereof.

Additional substrates suitable for the present invention include artificial (or synthetic) marble. Artificial marbles encompass cultured marble, onyx and solid surface materials typically comprising a resin matrix, said resin matrix comprising one or more fillers. Typically, cultured marble is made of a gel coating of unfilled unsaturated polyester on a substrate of a filled unsaturated polyester. The filler may be calcium carbonate or a similar material. Onyx typically consists of a gel coat of unfilled unsaturated polyester on a substrate of filled unsaturated polyester. The filler in this case is typically alumina trihydrate (ATH). Solid surface materials are typically filled resin materials and, unlike cultured marble or onyx, do not have a gel coat. Corian® material available from E.I. du Pont de Nemours and Company (DuPont), Wilmington, Del., is a solid surface material comprising an acrylic matrix filled with ATH. An additional solid surface DuPont material, known by the brand name Zodiaq®, is described as an engineered stone or artificial granite. Such materials are made from an unsaturated polyester matrix filled with quartz.

The articles of the present invention have antimicrobial peptides of the invention bound to or incorporated into a substrate. The use of antimicrobial peptides for rendering substrates antimicrobial provides many advantages to traditional molecules in that peptides exhibit rapid biocidal activity, broad spectrum activity, reduced environmental toxicity and a reduced likelihood of causing organisms to become resistant. Peptides can be bound to a substrate either physicochemically, or covalently. Physicochemical binding of oligopeptides to the substrate may occur by any one or combinations of the following forces: electrostatic, hydrogen bonding, and Van der Waals. Alternatively, oligopeptides may be bound to the substrate surface by a covalent bond. Additionally, antimicrobial peptides of the present invention can be incorporated into the polymer by mixing with the polymer, for example by dissolving the peptide and the polymer in a common solvent and casting or molding the peptide:polymer mixture into an article.

In one embodiment, the antimicrobial peptide is bound to the substrate by coating a substrate polymer with an aqueous or non-aqueous solution of the peptide, wherein the peptide is at concentration ranging from about 0.001 to about 20 weight percent. The peptide is contacted with the substrate polymer, and the peptide and polymer are optionally shaken at temperatures ranging from about −10° C. to about 150° C. for a period of time ranging from about 0.1 min to about 96 hrs. Preferably the peptide and polymer are shaken at a temperature of from about 25° C. to about 80° C. for a period of time ranging from about 1 min to about 24 hrs.

In another embodiment, the substrate polymer is primed to generate active groups that will bind to the antimicrobial peptide. Surface modification of the polymer may be achieved by a variety of techniques well known in the art including: oxidation, reduction, hydrolysis, plasma, and irradiation. Substrate polymers containing acid or base hydrolyzable groups such as polyesters, polyamides, and polyurethanes may be treated with acid or base first. Subsequently, the hydrolyzed polymer is brought into contact with an aqueous or non-aqueous solution of from about 0.001 to about 20 weight percent of the antimicrobial peptide. The peptide and the polymer may be shaken at temperatures ranging from about −10° C. to about 150° C. for a period of time ranging from about 0.1 min to about 96 hrs. Preferably the peptide and polymer are shaken at a temperature of from about 25° C. to about 80° C. for a period of time ranging from about 10 min to about 24 hrs.

In another embodiment, a commercial substrate polymer containing 1-50% active groups is brought into contact with an aqueous or non-aqueous solution comprising from about 0.001 to about 20 weight percent of the antimicrobial peptide.

After treatment with the antimicrobial peptide, the article may be washed, preferably with deionized water. Optionally, the article may then be dried via methods known in the art. Such methods include ambient air drying, oven drying, and air forced drying. In one preferred embodiment, the article is dried at about 50° C. to about 120° C., more preferably at about 50° C. to about 100° C., for about 15 min to about 24 hrs.

Articles comprising the polymer substrate of the present invention may be in the form of or comprise an extrudate, film, membrane, laminate, knit fabric, woven fabric, nonwoven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

The preferred articles of the present invention provide multiple uses, since many articles benefit from a reduction in microbial growth and a wide variety of substrates are included in the present invention. The following are examples of articles wherein it is desirable to reduce microbial growth in or on the article in the end-use for which the particular article is commonly used.

The articles of the invention include packaging for food, personal care (health and hygiene) items, and cosmetics. By "packaging" is meant either an entire package or a component of a package. Examples of packaging components include but are not limited to packaging film, liners, absorbent pads for meat packaging, tray/container assemblies, caps, adhesives, lids, and applicators. The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging, and caps.

Examples of applicators include those for lipstick, chapstick, and gloss; packages and applicators for eye cosmetics, such as mascara, eyeliner, shadow, dusting powder, bath powder, blusher, foundation and creams. These applicators are used to apply substances onto the various surfaces of the body and reduction of bacterial growth will be beneficial in such applications.

Other forms of packaging components included in the present invention include drink bottle necks, replaceable caps, non-replaceable caps, and dispensing systems; food and beverage delivery systems; baby bottle nipples and caps; and pacifiers. Where a liquid, solution or suspension is be applied, the package may be fashioned for application in a form for dispensing discrete drops or for spraying of droplets. The invention will also find use in pharmaceutical applications fashioned as inhalers.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; and machines for food cutting and slicing and components thereof. Where the surface of such equipment components is metal, the metal could be coated directly, or a coating of a polymer or functionalized polymer could first be applied to the metal surface. Alternatively, a film of such a polymer or functionalized polymer could be coated with an antimicrobial peptide of the invention and then applied to the equipment surface. Additional articles of the invention include foods and seeds.

Articles of the present invention can also be used in or as items of apparel, such as a swimsuit, undergarment, shoe component (for example, a woven or nonwoven shoe liner or insert), protective sports pad, child's garment. Articles of the invention also include protective medical garments or barrier materials, such as gowns, masks, gloves, slippers, booties, head coverings or drapes.

Articles of the present invention can also be used in or as medical materials, devices, or implants, such as bandages, adhesives, gauze strips, gauze pads, syringe holders, catheters such as peripheral IV catheters and central venus catheters comprised of either polyurethane or silicon, sutures, urinary catheter ostomy ports, orthopedic fixtures, orthopedic pins, pacemaker leads, defibrillator leads, ear canal shunts, vascular stents, cosmetic implants, ENT implants, staples, implantable pumps, hernia patches, plates, screws, blood bags, external blood pumps, fluid administration systems, heart-lung machines, dialysis equipment, artificial skin, artificial hearts, ventricular assist devices, hearing aids, vascular grafts, pacemaker components, hip implants, knee implants, and dental implants.

In the hygiene area, articles of the present invention include personal hygiene garments such as diapers, incontinence pads, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles of the present invention also include items intended for oral contact, such as a baby bottle nipple, pacifier, orthodontic appliance or elastic bands for same, denture material, cup, drinking glass, toothbrush, or teething toy.

Additional child-oriented articles that benefit from the present invention include baby bottles, baby books, plastic scissors, toys, diaper pails, and a container to hold cleansing wipes.

Household articles of the present invention include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

The current invention is also useful in reducing or preventing biofilm growth on the surface of separation membranes (for example, pervaporation, dialysis, reverse osmosis, ultrafiltration, and microfiltration membranes) comprised of polymer substrates of the invention.

In order to impart antimicrobial functionality to the products listed, the product can be treated with an antimicrobial peptide of the invention before it is manufactured, or after, or at any time during manufacture of the product. For example, in making an antimicrobial shower curtain, an antimicrobial peptide of the invention may be bound to or incorporated into the polymer substrate, followed by fashioning a shower curtain from the treated material. Alternatively, treatment of the polymer substrate with an antimicrobial peptide of the invention may be performed after the substrate is made into a shower curtain. It is believed that the antimicrobial properties of the material will not change significantly.

Antimicrobial substrates or articles prepared by methods of the invention exhibit antimicrobial functionality, wherein microbes are killed, or microbial growth is reduced or prevented. Antimicrobial activity of the antimicrobial substrate or article can be determined by using any of a number of methods well known in the art, such as the Shake Flask Test described in Example 4 of the present invention. Additional methods for determining antimicrobial activity are discussed in Tenover et al. (eds.), Manual of Clinical Microbiology, 7$^{th}$ Edition, Section VIII, 1999, American Society for Microbiology, Washington, D.C.

The present invention provides a method for killing, inhibiting, or preventing the growth of at least one microbe, the method comprising contacting the microbe with an effective amount of an antimicrobial peptide according to Formula (I) or Formula (II).

The present invention also provides antimicrobial compositions comprising at least one antimicrobial peptide, wherein the peptide is represented by Formula (I):

(B)-(U)-(Z-B-B-Z-Z-B-Z)$_n$-(U)     Formula (I)

wherein B, U and Z represent natural or unnatural amino acids and wherein:
- (a) Z is independently selected from Gly or a hydrophobic amino acid selected from the group consisting of Leu, Ile, Trp, Phe, Val, Met, and Ala; and
  - (i) when Z is Gly, the Gly residues representing Z must be minimally 7 amino acid residues apart; and
  - (ii) no more than six sequential hydrophobic Z residues may occur in the antimicrobial peptide;
- (b) B is a cationic amino acid independently selected from the group consisting of Lys, Arg, His, Orn, Har, and Dbu; and
- (c) U is Gly, Cys, or Cys(R), wherein R is a protecting group on the Cys thiol;
- (d) n=2-8; and
- (e) the N-terminal B residue, and the N-terminal or C-terminal U residue, are optionally part of the antimicrobial peptide.

In another embodiment the invention provides antimicrobial compositions comprising at least one antimicrobial peptide, wherein said peptide is represented by Formula (II):

(B)-Cys-(Z-B-B-Z-Z-B-Z)$_n$-Cys     Formula (II)

wherein B and Z represent natural or unnatural amino acids and wherein:
- (a) Z is independently selected from Gly or a hydrophobic amino acid selected from the group consisting of Leu, Ile, Trp, Phe, Val, Met, and Ala; and
  - (i) when Z is Gly, the Gly residues representing Z must be minimally 7 amino acid residues apart; and
  - (ii) no more than six sequential hydrophobic Z residues may occur in the antimicrobial peptide;
- (b) B is a cationic amino acid independently selected from the group consisting of Lys, Arg, His, Orn, Har, and Dbu;
- (c) n=2-5;
- (d) the N-terminal B residue is optionally part of the antimicrobial peptide; and
- (e) the antimicrobial peptide contains a disulfide bridge formed intramolecularly between the Cys residues.

The antimicrobial peptide of Formula (I) or Formula (II) comprises from about 0.00001% to about 20% by weight of the composition. In another embodiment of the invention the antimicrobial peptide comprises from about 0.0001% to about 10% by weight of the composition. In still another embodiment of the invention the antimicrobial peptide comprises from about 0.001% to about 5% by weight of the composition.

The present invention also comprises methods for killing, inhibiting, or preventing the growth of at least one microbe, the method comprising administering an effective amount of an antimicrobial composition comprising at least one antimicrobial peptide wherein said antimicrobial peptide is represented by Formula (I):

(B)-(U)-(Z-B-B-Z-Z-B-Z)$_n$-(U)     Formula (I)

wherein B, U, and Z represent natural or unnatural amino acids and wherein:

(a) Z is independently selected from Gly or a hydrophobic amino acid selected from the group consisting of Leu, Ile, Trp, Phe, Val, Met, and Ala; and
  (i) when Z is Gly, the Gly residues representing Z must be minimally 7 amino acid residues apart; and
  (ii) no more than six sequential hydrophobic Z residues may occur in the antimicrobial peptide;
(b) B is a cationic amino acid independently selected from the group consisting of Lys, Arg, His, Orn, Har, and Dbu; and
(c) U is Gly, Cys or Cys(R), wherein R is a protecting group on the Cys thiol;
(d) n=2-8; and
(e) the N-terminal B residue, and the N-terminal or C-terminal U residue, are optionally part of the antimicrobial peptide.

The present invention also comprises methods for killing, inhibiting, or preventing the growth of at least one microbe, the method comprising administering an effective amount of an antimicrobial composition comprising at least one antimicrobial peptide wherein said antimicrobial peptide is represented by Formula (II):

wherein B and Z represent natural or unnatural amino acids and wherein:

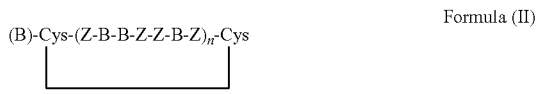

Formula (II)

(a) Z is independently selected from Gly or a hydrophobic amino acid selected from the group consisting of Leu, Ile, Trp, Phe, Val, Met, and Ala; and
  (i) when Z is Gly, the Gly residues representing Z must be minimally 7 amino acid residues apart; and
  (ii) no more than six sequential hydrophobic Z residues may occur in the antimicrobial peptide;
(b) B is a cationic amino acid independently selected from the group consisting of Lys, Arg, His, Orn, Har, and Dbu;
(c) n=2-5;
(d) the N-terminal B residue is optionally part of the antimicrobial peptide; and
(e) the antimicrobial peptide contains a disulfide bridge formed intramolecularly between the Cys residues.

The present invention also comprises methods for killing, inhibiting, or preventing the growth of at least one microbe, the method comprising bringing at least one microbe into contact with a substrate coated with an effective amount of at least one antimicrobial peptide selected from peptides of Formula (I) or Formula (II).

EXAMPLES

The present invention is further defined in the following Examples, in which all parts and percentages are by weight unless otherwise indicated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Materials

4-Hydroxymethylphenoxymethyl (HMP) resin, preloaded HMP resin with various amino acids, and 9-fluorenyl-methoxycarbonyl (Fmoc) amino acids with fully protected side chains were purchased from Applied Biosystems (Foster City, Calif.). The lysine side chain was protected by a t-butyloxycarbonyl group (Boc), and the cysteine side chain was protected with an S-acetamidomethyl (Acm) group. Other reagents used for peptide synthesis included trifluoroacetic acid (Aldrich; Milwaukee, Wis.), piperidine (Aldrich), N-methyl-pyrrolidinone (NMP) (VWR; West Chester, Pa.), 1-hydroxybenzotriazole (HOBt) (Applied Biosystems; Foster City, Calif.) and N-[(1H-benzotriazol-1-yl)(dimethylamino)methylene]-N-methylmethanaminium hexafluorophosphate N-oxide (HBTU) (Applied Biosystems); these chemicals were used without further purification.

In the following examples, "milliliter" is abbreviated "mL", "microliter" is abbreviated "μL", "microgram" is abbreviated "μg", "hour(s)" is abbreviated "hr(s)", "minute(s)" is abbreviated "min(s)", and "Centigrade" is abbreviated "C".

Example 1

Peptide Synthesis

All peptides were synthesized using standard solid phase peptide synthesis methodology. The peptides were synthesized using an Applied Biosystems 433A Peptide Synthesizer, using 9-fluorenylmethoxycarbonyl (Fmoc)-protected amino acids. Lysine side chains were protected by Boc. For peptides with C-terminal carboxylic acids, pre-loaded 4-hydroxymethylphenoxymethyl (HMP) resins loaded with the desired Fmoc-protected amino acids were used. For peptides with C-terminal amides, an Fmoc-amide resin (Applied Biosystems) was used. The subsequent amino acids were coupled by in-situ activation of the carboxylic acid group using a dimethylformamide solution of HOBt and HBTU. The peptides were cleaved from the resins by shaking the resins in 95:2.5:2.5 trifluoroacetic acid (TFA):water:triisopropylsilane at room temperature for two hours. The peptides were triturated from cold ether, and collected by filtration. The crude peptides were purified by preparative HPLC (Varian; Palo Alto, Calif.) on a C18 reverse phase column to >95% purity. The purified peptides were analyzed by analytical HPLC and shown to be >97% pure. Electrospray mass spectroscopy was carried out to confirm the composition and molecular mass of the peptides.

General Procedure for the Oxidation of Cysteine Containing Peptides:

Acm-protected oligopeptides (such as SEQ ID NOs 8 and 9, 20 mg) were dissolved in 5 mL acetic acid/water (4:1 v:v) to give a 2 mM peptide solution. Iodine (24 mg) was added to this solution, and the reaction mixture was stirred for two hours. Water (10 mL) was then added to the reaction mixture. The solution was extracted with chloroform (5×10 mL) and the organic layer was lyophilized. The crude cyclized peptide was purified to >95% purity by RP-HPLC using a C18 column, and the composition was confirmed by electrospray mass spectroscopy.

Example 2

Antimicrobial Assay

The minimal inhibitory concentration (MIC) for the peptides was determined in sterile microtiter plates in a final volume of 200 μL using Trypticase Soy Broth (TSB; Difco Laboratories, Detroit, Mich.) as the growth medium. Serial two-fold dilutions of the peptide stock were made in the plate wells such that concentrations ranged from 512 to 2 μg/mL in a volume of 100 μL. Each well was then inoculated with 100 μL of a dilute suspension of bacteria in TSB yielding a final concentration of $1 \times 10^4$ bacteria/mL. The final peptide concentrations ranged from 1 mg/mL to 256 μg/mL. The assay plates were incubated at 37° C. for 24 hours inside a Bioscreen C microtitre plate reader (Thermo Labsystems; Vantaa, Finland). Optical Density (OD) of the medium at 600 nm was recorded every 20 minutes to monitor cell growth. The lowest concentration of peptide preventing bacterial growth during the 24 hr period was defined as the MIC. Table 1 shows the antimicrobial activity of oligopeptides against *E. coli*. Table 2 shows the antimicrobial activity of oligopeptides against bacteria and yeast.

TABLE 1

Antimicrobial activity of oligopeptides vs. *E. coli* ATCC 25922.

| SEQ ID NO. | Peptide | MIC (μg/mL) |
|---|---|---|
| 1 | KGLKKLLKGLKKLLKL | 4 |
| 40 | KGLKKGLKGLKKLLKL | 256 |
| 17 | KC(Acm)LKKLLKGLKKLLKLC(Acm) | 4 |
| 31 | KCLKKLLKGLKKLLKLC | 16 |
| 25 | C(Acm)LKKLLKGLKKLLKLC(Acm) | 8 |
| 38 | CLKKLLKGLKKLLKLC | 32 |

Example 3

Hemolysis Assay

The experimental procedure was based, in part, upon O'Leary et al. (ASTM Standard F756-93, Assessment of hemolytic properties of materials, ASTM (1969)), and United States Pharmacopeia, $24^{th}$ Edition (United States Pharmacopeial Convention, Inc., Rockville, Md., (2000)). The presence of hemolytic material in contact with blood may lyse erythrocytes. The hemoglobin liberated is a direct function of the number of erythrocytes hemolyzed. A quantitative determination of partial hemolysis was made by comparing the hemoglobin level as determined spectrophotometrically in the samples containing test peptide to hemoglobin liberated under control conditions of 0% and 100% hemolysis.

An aliquot of human blood (0.08 mL) was added to each of the test peptide or control substance tubes; the concentration of test peptide was 10 μM. The tubes were sealed, gently inverted, and incubated under static conditions (no agitation) for four hours at 37±2° C. At the end of the incubation period, the tubes were centrifuged at approximately 100×g for 15 minutes at room temperature. An aliquot of each supernatant was transferred to clean spectrophotometer cuvettes and the OD was read at a wavelength of 545 nm. The hemolysis was determined as follows:

$$\text{Hemolytic index } (\%) = \frac{\text{Replicate Mean } OD \text{ test sample} - \text{Group Mean } OD \text{ negative control} \times 100}{\text{Group Mean } OD \text{ 100\% hemolysis control} - \text{Group Mean } OD \text{ negative control}}$$

The results are shown in Table 2.

TABLE 2

Antimicrobial activity of oligopeptides vs. bacteria and yeast. The ATCC number for each strain appears under the organism name. The values represent MIC values in μg/mL. (NA: Not tested; Expt.: experiment)

| SEQ ID NO. | Peptide | E. coli 25922 Expt. #1 | E. coli 25922 Expt. #2 | S. aureus 29213 | K. pneumoniae 700603 | P. aeruginosa 27853 | C. albicans 10231 |
|---|---|---|---|---|---|---|---|
| 5 | KGLKKLLKLLKKGLKL | <=4* | 2 | 32+ | 8-16 | 8 | NA |
| 3 | KGLKKLLKLGKKLLKL | <=4* | 2 | 64-128 | 8 | 8 | NA |
| 41 | KGLKKLLKALKKLLKL | <=4* | 2 | 64 | 16 | 8-16 | NA |
| 42 | KGLKKLGKLLKKLLKL | <=4* | 2 | 64 | 4-8 | 8-16 | NA |
| 2 | KGLKKGLKLLKKLLKL | <=4* | 2 | 64-128 | 4-8 | 8 | NA |
| 43 | KGGKKLLKGLKKLLKL | <=4* | 2 | 256 | 64 | 16 | NA |
| 1 | KGLKKLLKGLKKLLKL | NA | 2-4 | 8 | 8-16 | 2 | 128 |

*4 μg/mL was the lowest concentration tested in this experiment.

TABLE 2

Hemolytic Index of Peptides.

| SEQ ID NO. | Peptide | Hemolytic Index |
|---|---|---|
| 1 | KGLKKLLKGLKKLLKL | 0-2 |
| 13 | KGLKKLLKLLKKLLKL | 20-40 |

Example 4

Shake Flask Test

Antimicrobial activity of the peptide immobilized on polymer substrates was evaluated in a Shake Flask Test. Test substance (polymer with immobilized peptide) or control substance (polymer alone) (50 mg suspended in 0.6M phosphate buffer (pH 7)) was added to a sterile culture plate well; a dilute suspension of bacteria ($1 \times 10^5$ cells/mL final concentration in the well) in 0.6 mM phosphate buffer was added to the well for a final volume of 5 mL. The plate was shaken on a platform shaker at room temperature. At specified times (4 hours and 24 hours), an aliquot was removed from the culture plate (0.1 mL, in triplicates), and serial dilutions ranging from 1 to 100 fold were made for enumeration of cells on trypticase soy agar (TSA) plates. The TSA plates were incubated for 20 hr at 37° C., and the number of colony forming units (CFU) per mL was determined.

Example 5

Antimicrobial Peptide Immobilization on Polyester

Polyester fabric (poly(ethylene terephthalate)) was immersed in a 10% sodium hydroxide solution for 90 min and then washed with deionized water. The fabric was then treated with a 10% hydrogen chloride solution for 20 min, washed with deionized water, and air-dried. The fabric was then extracted three times with methylene chloride.

The fabric (100 mg) was weighed into a 20 mL vial. Oligopeptide (SEQ ID NO:1, 10 mg) in 5.0 mL of 50 mM sodium phosphate buffer (pH 6.2) was then added to the vial. The mixture was shaken at 70° C. for 16 hrs. The mixture was allowed to cool to room temperature for 20 min, and then the excess solution was decanted. The fabric was washed with distilled, deionized water (4×10 mL with 15 min agitation), and dried in an oven at 90° C. for 30 min. The biological activity of the fabric sample against E. coli ATCC #25922 was evaluated using the Shake Flask Test (see Example 4), and a 4.6 log reduction in E. coli CFU/mL after 4 hours was observed.

Example 6

Antimicrobial Peptide Immobilization on Silk

Silk fiber was extracted three times with methylene chloride prior to use. Oligopeptide (SEQ ID NO:1) (10 mg) and silk fiber (100 mg) were suspended in 5.0 mL of 50 mM sodium phosphate buffer at pH 6.2. The mixture was shaken at 70° C. for 16 hrs. The mixture was allowed to cool to room temperature for 20 min, and the excess solution was decanted. The fiber was washed with distilled, deionized water (4×10 mL with 15 min agitation), dried in an oven at 90° C. for 30 min. The biological activity of the fabric sample against E. coli ATCC #25922 was evaluated using the Shake Flask Test (see Example 4), and a 4.6 log reduction in E. coli CFU/mL after 4 hours was observed.

Example 7

Antimicrobial Peptide Immobilization on EUPERGIT® Resin

The matrix of EUPERGIT™ is a copolymerisate of methacrylamide, N,N'-methylene-bis(methacrylamide) and monomers containing oxirane groups. The oxirane groups function as the reactive components and covalently bind proteins or peptides via their amino and sulfhydryl groups.

EUPERGIT® resin (100 mg EUPERGIT®, Sigma, 150 μm particle size) was charged into a polypropylene vial. Oligopeptide (SEQ ID NO:1, 10 mg) in 1 mL of 1 M phosphate buffer (pH 7.7) was added to the dry resin, followed by the addition of 1.5 mL of 1.0 M sodium phosphate buffer (pH 7.7). The mixture was shaken on a laboratory rotator at room temperature for 15 hr. The vial was then centrifuged and the supernantant was decanted. Phosphate buffer (0.1M (pH 7.7); 1.5 mL) was added to the resin; the resin was shaken for 30 min and then centrifuged and the buffer was decanted. This washing procedure was repeated two additional times. The washed resin was then shaken with a 20% ethanolamine solution in 1.0 M phosphate buffer (pH 7.7) at room temperature overnight. The resin was then washed four times with 0.1 M phosphate buffer (pH 7.7), followed by washing with water (4×). The biological activity of the sample against E. coli ATCC #25922 was evaluated using the Shake Flask Test (see Example 4), and a 4.6 log reduction in E. coli CFU/mL after 4 hours was observed.

Example 8

Antimicrobial Peptide Immobilization on Polyurethane

Polyether polyurethane (400 mg, Elasthane (™) 75 D, The Polymer Technology Group, Berkeley, Calif.) is dissolved in 0.5 mL of dimethylformamide. To this mixture is added 20 mg of oligopeptide. The mixture is agitated on a vortexer, and the solution is drawn over a glass plate to form a polyurethane film.

Example 9

Antimicrobial Peptide Immobilization on Polyester

Polyester fabric (poly(ethylene terephthalate)) was immersed in a 10% sodium hydroxide solution for 90 min and then washed with deionized water. The fabric was then treated with a 10% hydrogen chloride solution for 20 min, washed with deionized water, and air-dried. The fabric was then extracted three times with methylene chloride.

The fabric (100 mg) is weighed into a 20 mL vial. Oligopeptide (SEQ ID NO:1, 10 mg) in 5.0 mL of 50 mM sodium phosphate buffer (pH 5) is added to the vial, followed by 10 mg of N-(3-Dimethylaminopropyl)-N'-ethylcarbodiimide hydrochloride (EDC; Sigma-Aldrich, St. Louis, Mo.) hydrochloride. The mixture is shaken at room temperature for 5 hrs. The solution is decanted. The fabric is washed with distilled, deionized water (4×10 mL with 15 min agitation), and dried in an oven at 90° C. for 30 min.

Example 10

Antimicrobial Peptide Immobilization on Polyester

Polyester fabric (poly(ethylene terephthalate)) is immersed in a 10% sodium hydroxide solution for 90 min and then is washed with deionized water. The fabric is treated with a 10% hydrogen chloride solution for 20 min, washed with deionized water, and air-dried. The fabric is then extracted three times with methylene chloride.

The fabric (200 mg) is suspended in 20 mL 2 mM EDC and 5 mM 1-hydroxy-2,5-dioxo-3-pyrrolidinesulfonic acid, monosodium salt hydrate, in 0.1 M 2-(N-morpholino)ethane sulfonic acid buffer at pH 4.7. The mixture is stirred at room temperature for 1 hr. The fabric is removed and is suspended in 4 mL of 0.1 M sodium phosphate buffer, pH 7.5. To this is added 10 mg of oligopeptide (SEQ ID:1). The mixture is stirred at room temperature for four hours. The mixture is decanted and the fabric is washed with water (4×10 mL), and is oven dried at 60° C. for 1 hour.

Example 11

Antimicrobial Peptide Immobilization on Polyester

Polyester fabric (poly(ethylene terephthalate)) is immersed in a 10% sodium hydroxide solution for 90 min and then is washed with deionized water. The fabric is treated with a 10% hydrogen chloride solution for 20 min, washed with deionized water, and air-dried. The fabric is then extracted three times with methylene chloride.

50 mg of the above polyester fabric is immersed in 5 mL 50 mM phosphate buffer (pH 6.0). To this is added 5 mg of oligopeptide (SEQ ID:1), EDC (10 mg) and HOBT (FW 153.2, 8 mg, 0.052 mmol). The mixture is stirred at room temperature for 4 hrs. The excess reagent is decanted, and the material is rinsed with ethanol (3×10 mL×15 minutes) followed by water (4×10 mL×15 minutes), and is dried in an oven at 90° C. for 30 min.

---

The invention claimed is:

1. A peptide represented by Formula I:

(B)-(U)-(Z-B-B-Z-Z-B-Z)$_n$-(U)     Formula (I)

wherein B, U and Z represent natural or unnatural amino acids and wherein:
(a) the amino acids of each (ZBBZZBZ) unit are determined independently;
(b) in each (ZBBZZBZ) unit, Z is independently selected from Gly or a hydrophobic amino acid selected from the group consisting of Leu, Ile, Trp, Phe, Val, Met, and Ala; and
   (i) wherein in at least one (ZBBZZBZ) unit, one Z is Gly,
   (ii) when Z is Gly, the Gly residues representing Z must be minimally 7 amino acid residues apart; and
   (iii) no more than six sequential hydrophobic Z residues may occur in the peptide;
(c) B is a cationic amino acid independently selected from the group consisting of Lys, Arg, His, Orn, Har, and Dbu; and
(d) U is Gly, Cys or Cys(R), wherein R is a protecting group on the Cys thiol;
(e) n=2-8; and
(f) the N-terminal B residue, and the N-terminal or C-terminal U residue, are optionally part of the peptide.

2. A peptide represented by Formula II:

(B)-Cys-(Z-B-B-Z-Z-B-Z)$_n$-Cys     Formula (II)

wherein B and Z represent natural or unnatural amino acids and wherein:
(a) the amino acids of each (ZBBZZBZ) unit are determined independently;
(b) in each (ZBBZZBZ) unit, Z is independently selected from Gly or a hydrophobic amino acid selected from the group consisting of Leu, Ile, Trp, Phe, Val, Met, and Ala; and
   (i) wherein in at least one (ZBBZZBZ) unit, one Z is Gly,
   (ii) when Z is Gly, the Gly residues representing Z must be minimally 7 amino acid residues apart; and
   (iii) no more than six sequential hydrophobic Z residues may occur in the peptide;
(c) B is a cationic amino acid independently selected from the group consisting of Lys, Arg, His, Orn, Har, and Dbu;
(d) n=2-5;
(e) the N-terminal B residue is optionally part of the peptide; and
(f) the peptide contains a disulfide bridge formed intramolecularly between the Cys residues.

3. The peptide of claim 1 or claim 2 wherein n=2.

4. The peptide of claim 1 or claim 2 wherein the peptide is modified on the N-terminus with an acetyl group, modified on the C-terminus with an amide, or combinations thereof.

5. The peptide of claim 1 or claim 2 wherein the N-terminal Z is deleted.

6. The peptide of claim 1 or claim 2 wherein the C-terminal Z and/or B is deleted.

7. The peptide of claim 1 or claim 2 wherein said peptide is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, and SEQ ID NO:42.

8. A composition comprising at least one peptide wherein the peptide is represented by Formula (I):

(B)-(U)-(Z-B-B-Z-Z-B-Z)$_n$-(U)     Formula (I)

wherein B, U and Z represent natural or unnatural amino acids and wherein:
(a) the amino acids of each (ZBBZZBZ) unit are determined independently;

(b) in each (ZBBZZBZ) unit, Z is independently selected from Gly or a hydrophobic amino acid selected from the group consisting of Leu, Ile, Trp, Phe, Val, Met, and Ala; and
   (i) wherein in at least one (ZBBZZBZ) unit, one is Gly;
   (ii) when Z is Gly, the Gly residues representing Z must be minimally 7 amino acid residues apart; and
   (iii) no more than six sequential hydrophobic Z residues may occur in the peptide;
(c) B is a cationic amino acid independently selected from the group consisting of Lys, Arg, His, Orn, Har, and Dbu; and
(d) U is Gly, Cys or Cys(R), wherein R is a protecting group on the Cys thiol;
(e) n=2-8; and
(f) the N-terminal B residue, and the N-terminal or C-terminal U residue, are optionally part of the peptide.

9. A composition comprising at least one peptide wherein the peptide is represented by Formula II:

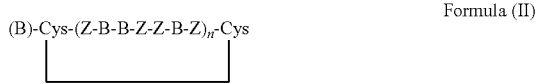

Formula (II)

wherein B and Z represent natural or unnatural amino acids and wherein:
(a) the amino acids of each (ZBBZZBZ) unit are determined independently;
(b) in each (ZBBZZBZ) unit, Z is independently selected from Gly or a hydrophobic amino acid selected from the group consisting of Leu, Ile, Trp, Phe, Val, Met, and Ala; and
   (i) wherein in at least one (ZBBZZBZ) unit, one Z is Gly,
   (ii) when Z is Gly, the Gly residues representing Z must be minimally 7 amino acid residues apart; and
   (iii) no more than six sequential hydrophobic Z residues may occur in the peptide;
(c) B is a cationic amino acid independently selected from the group consisting of Lys, Arg, His, Orn, Har, and Dbu;
(d) n=2-5;
(e) the N-terminal B residue is optionally part of the peptide; and
(f) the peptide contains a disulfide bridge formed intramolecularly between the Cys residues.

10. A substrate comprising:
(i) a polymer selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, mixtures thereof, and functionalized polymers thereof; (ii) ceramics; (iii) glass; (iv) metal, (v) metal oxides, or (vi) composites comprising at least one latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, mixtures thereof, and functionalized polymers thereof and at least one of the group consisting of (iii) glass; (iv) metal and (v) metal oxides, and
a peptide of claims 1 or 2 bound thereto.

11. The substrate of claim 10 wherein the polymer is a functionalized polymer.

12. A process for preparing a peptide comprising:
(a) synthesizing an oligonucleotide corresponding to the amino acid sequence of an peptide according to claims 1 or 2;
(b) operably linking the oligonucleotide of step (a) to a promoter in a suitable vector;
(c) introducing the product of step (b) into a suitable host cell;
(d) culturing the suitable host cell under conditions in which the peptide is produced; and
(e) optionally recovering the peptide produced in step (d).

13. An article comprising the substrate of claim 10.

14. A medical material, device, or implant comprising the substrate of claim 10.

15. The medical material, device, or implant of claim 14 selected from the group consisting of bandages, adhesives, gauze strips, gauze pads, syringe holders, catheters, sutures, urinary catheter ostomy ports, orthopedic fixtures, orthopedic pins, pacemaker leads, defibrillator leads, ear canal shunts, vascular stents, cosmetic implants, ENT implants, staples, implantable pumps, hernia patches, plates, screws, blood bags, external blood pumps, fluid administration systems, heart-lung machines, dialysis equipment, artificial skin, artificial hearts, ventricular assist devices, hearing aids, vascular grafts, pacemaker components, hip implants, knee implants, and dental implants.

16. The medical material, device, or implant of claim 14 comprised of polyurethane or silicon.

17. The medical device of claim 14 being a central venous or peripheral catheter.

18. The article of claim 13 in the form of a extrudate, film, membrane, laminate, knit fabric, woven fabric, nonwoven fabric, fiber, filament, yarn, pellet, coating, or foam.

19. The article of claim 18, wherein the article has been blown, solution cast, laminated, injection molded, extruded, blow molded, thermoformed, knit, woven, or spun.

20. A package or packaging component comprising the substrate of claim 10.

21. The package of claim 20 selected from the group consisting of a bottle, box, jar, can, bag, close-ended tube, or cosmetics package.

22. The package of claim 21 containing a cosmetic, a personal hygiene material, a healthcare material, or a combination thereof.

23. The packaging component of claim 22 in the form of a liner, lid, adhesive, replaceable or disposable container cap, film, tray/container assembly, absorbent pad for meat packaging, applicator, drink bottle neck, food dispensing system, or beverage dispensing system.

24. The package of claim 23 comprising an inhaler.

25. The package of claim 21 containing a food or a beverage.

26. A food or seed comprising the peptide of claims 1 or 2.

27. A baby bottle, baby book, plastic scissors, toy, diaper pail, or container for cleansing wipes comprising the substrate of claim 10.

28. An article intended for oral contact, the article comprising the substrate of claim 10.

29. The article of claim 28 which is a baby bottle nipple, pacifier, orthodontic appliance or component thereof, denture material, cup, drinking glass, toothbrush, or teething toy.

30. A tampon or tampon applicator comprising the substrate of claim 10.

31. A personal cleansing wipe, baby wipe, or cosmetic wipe comprising the substrate of claim 9.

32. A personal hygiene garment comprising the substrate of claim 10.

33. The personal hygiene garment of claim 32 wherein said personal hygiene garment is a diaper, incontinence garment, or sanitary napkin.

34. Food handling and processing equipment comprising the substrate of claim 10.

35. The food handling and processing equipment of claim 34, selected from the group consisting of a conveyor belt assembly and components thereof; temporary and permanent food preparation surfaces; equipment for mixing, grinding, crushing, rolling, pelletizing, and extruding and components thereof; heat exchangers and their components; and machines for food cutting and slicing and components thereof.

36. An item of apparel comprising the substrate of claim 10.

37. The item of apparel of claim 35 in the form of a swimsuit, sportswear, active wear, protective sports pad, undergarment, shoe component, shoe insert, child's garment.

38. The item of apparel of claim 37 wherein the shoe component is a woven or nonwoven liner or an insert.

39. A protective medical garment or barrier material comprising the substrate of claim 10 in the form of a gown, mask, glove, slipper, bootie, head covering or drape.

40. A household article comprising the substrate of claim 10.

41. The household article of claim 40 selected from the group consisting of fiberfill, bedding, bed linens, window treatments, carpet and flooring components, upholstery components, sheets, automotive wipes, nonwoven dryer sheets, laundry softener-containing sheets, household cleaning wipes, counter wipes, towels, washcloths, dust cloths, mops, tablecloths, shower curtains, telephones and cellular phones, and wall, counter and floor surfaces.

42. A separation membrane comprising the substrate of claim 10.

43. A process for preparing an substrate or article, the process comprising the steps of:
    (a) contacting the substrate or article with a solution comprising an peptide according to claims 1 or 2;
    (b) optionally washing the product of step (a); and
    (c) optionally drying the product of step (b).

44. The process according to claim 43 wherein step (a) is performed for a period of time ranging from about 0.1 mm to about 96 hrs.

45. The process according to claim 44 wherein step (a) is carried out at a temperature ranging from about −10° C. to about 150° C.

46. A peptide represented by SEQ ID NO:43 or SEQ ID NO: 11.

* * * * *